United States Patent
Shannon et al.

(10) Patent No.: US 8,940,323 B2
(45) Date of Patent: *Jan. 27, 2015

(54) TISSUE PRODUCTS HAVING A COOLING SENSATION WHEN CONTACTED WITH SKIN

(75) Inventors: Thomas Gerard Shannon, Neenah, WI (US); Frank P. Abuto, Johns Creek, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1237 days.

This patent is subject to a terminal disclaimer.

(21) Appl. No.: 12/130,026

(22) Filed: May 30, 2008

(65) Prior Publication Data

US 2009/0297586 A1    Dec. 3, 2009

(51) Int. Cl.
| | | |
|---|---|---|
| *A61K 8/02* | (2006.01) | |
| *A61K 8/31* | (2006.01) | |
| *A61F 13/511* | (2006.01) | |
| *A61F 13/513* | (2006.01) | |
| D21H 27/00 | (2006.01) | |
| *D21H 17/04* | (2006.01) | |
| *D21H 17/06* | (2006.01) | |
| *D21H 21/14* | (2006.01) | |

(52) U.S. Cl.
CPC ............ *D21H 27/002* (2013.01); *D21H 17/04* (2013.01); *D21H 17/06* (2013.01); *D21H 21/14* (2013.01)
USPC ........... 424/443; 424/401; 424/402; 162/124; 162/135

(58) Field of Classification Search
None
See application file for complete search history.

(56) References Cited

U.S. PATENT DOCUMENTS

| | | | |
|---|---|---|---|
| 2,721,554 A | * | 10/1955 | Joa ............................... 604/382 |
| 3,585,104 A | | 6/1971 | Kleinert |
| 4,514,345 A | | 4/1985 | Johnson et al. |
| 4,528,239 A | | 7/1985 | Trokhan |
| 4,594,130 A | | 6/1986 | Chang et al. |
| 4,793,898 A | | 12/1988 | Laamanen et al. |
| 5,098,522 A | | 3/1992 | Smurkoski et al. |
| 5,260,171 A | | 11/1993 | Smurkoski et al. |
| 5,275,700 A | | 1/1994 | Trokhan |

(Continued)

FOREIGN PATENT DOCUMENTS

| | | |
|---|---|---|
| WO | WO 99/34057 | 7/1999 |
| WO | WO 00/66835 | 11/2000 |
| WO | WO 2006/007564 | 1/2006 |

OTHER PUBLICATIONS

TAPPI Test Method T411 om-89, "Thickness (caliper) of paper, paperboard, and combined board", Revised 1989.

(Continued)

*Primary Examiner* — Lakshmi Channavajjala
(74) *Attorney, Agent, or Firm* — Dority & Manning, P.A.

(57) ABSTRACT

Wiping products, such as facial tissues, contain a temperature change composition that can provide a cooling sensation when contacted with the skin of a user. The temperature change composition, for instance, can contain one or more phase change agents that undergo a phase change at slightly elevated temperatures. The phase change agents, in one embodiment, can have a relatively high heat of fusion. When undergoing a phase change, the phase change agents absorb heat and thereby provide a cooling feeling to the skin of a user. In one embodiment, the phase change agent comprises a straight chain hydrocarbon. Hydrocarbons useful as phase change agents include an octadecane, a nonadecane, a heptonoate, or mixtures thereof.

28 Claims, 3 Drawing Sheets

(56) References Cited

U.S. PATENT DOCUMENTS

| | | | |
|---|---|---|---|
| 5,328,565 A | 7/1994 | Rasch et al. | |
| 5,334,289 A | 8/1994 | Trokhan et al. | |
| 5,431,786 A | 7/1995 | Rasch et al. | |
| 5,496,624 A | 3/1996 | Stelljes, Jr. et al. | |
| 5,500,277 A | 3/1996 | Trokhan et al. | |
| 5,514,523 A | 5/1996 | Trokhan et al. | |
| 5,529,665 A | 6/1996 | Kaun | |
| 5,554,467 A | 9/1996 | Trokhan et al. | |
| 5,566,724 A | 10/1996 | Trokhan et al. | |
| 5,595,628 A | 1/1997 | Gordon et al. | |
| 5,624,790 A | 4/1997 | Trokhan et al. | |
| 5,628,876 A | 5/1997 | Ayers et al. | |
| 6,238,682 B1 * | 5/2001 | Klofta et al. | 424/402 |
| 6,428,794 B1 | 8/2002 | Klofta et al. | |
| 6,749,860 B2 * | 6/2004 | Tyrrell et al. | 424/404 |
| 6,855,410 B2 * | 2/2005 | Buckley | 428/311.11 |
| 6,860,967 B2 * | 3/2005 | Baumoller et al. | 162/158 |
| 6,896,766 B2 | 5/2005 | Sarbo et al. | |
| 6,949,167 B2 | 9/2005 | Shannon et al. | |
| 7,008,507 B2 | 3/2006 | Urlaub et al. | |
| 7,351,308 B2 * | 4/2008 | Urlaub et al. | 162/135 |
| 7,582,577 B2 * | 9/2009 | Vinson | 442/100 |
| 8,039,011 B2 * | 10/2011 | Flugge-Berendes et al. | 424/401 |
| 2004/0234561 A1 * | 11/2004 | Ansmann et al. | 424/401 |
| 2005/0136765 A1 | 6/2005 | Shannon | |
| 2005/0238701 A1 | 10/2005 | Kleinwaechter | |
| 2005/0274470 A1 | 12/2005 | Shannon et al. | |
| 2006/0029628 A1 * | 2/2006 | Kleinwaechter | 424/402 |
| 2008/0045913 A1 | 2/2008 | Johnson et al. | |
| 2008/0188560 A1 * | 8/2008 | Mohammadi et al. | 514/546 |

OTHER PUBLICATIONS

International Search Report PCT/IB2009/051515, filed Apr. 9, 2009 and mailed Oct. 30, 2009.

Solid-liquid phase behavior of binary fatty acid mixtures 3. Mixtures of oleic acid with capric acid (decanoic acid) and caprylic acid (octanoic acid), Inoue, T., et al., Chemistry and Physics of Lipids, vol. 132 (2004), pp. 225-234.

* cited by examiner

TISSUE PRODUCTS HAVING A COOLING SENSATION WHEN CONTACTED WITH SKIN

BACKGROUND

Various different healthcare and cosmetic products are applied to the skin in order to provide various benefits. Such products can include, for instance, lotions, creams, moisturizers, and the like. In some circumstances, the products are intended to provide a cooling feeling or cooling sensation to the skin once applied. Existing products typically provide skin cooling by combining skin cooling agents with other substances.

There are several different means to impart a cooling sensation to the skin, including using evaporation, neurosensory components, or physical agents such as phase change agents. One example of a cooling agent is menthol which provides cooling in the form of a physiological or neurosensory effect on nerve endings in the human body that sense temperature. The cooling sensation from menthol is not due to latent heat of evaporation but appears to be the result of direct stimulus on the cold receptors at the nerve endings.

The use of phase change agents to impart cooling is discussed, for instance, in PCT International Publication No. WO 2006/007564 entitled "Cosmetic Compositions and Methods for Sensory Cooling", which is incorporated herein by reference. In the '564 application, a skincare cosmetic composition is described in the form of a lotion that is intended for use in after-sun products, after-shave products, and body moisturizing products. The lotion is intended to create a cooling sensation on the skin by incorporating into the lotion components that absorb heat from the skin. In particular, ingredients are incorporated into the lotion that absorb heat from the skin and melt. The components have a relatively high heat of fusion which is defined in the '564 application as the heat absorbed by unit of mass of a solid chemical element at its melting point in order to convert the solid into a liquid at the same temperature. The '564 application states that the relatively high heat of fusion facilitates the absorption of heat from the skin to aid in melting the solid ingredient when applied to the skin, thereby cooling the skin temperature.

In the above described products, the products are intended to be directly contacted with the skin. The present disclosure, on the other hand, is directed to using cooling agents, such as phase change agents, in dry tissue or similar dry wiping products for cooling the skin during use of the product. In one embodiment, the cooling agents can be incorporated into the product without substantially contacting the skin and/or transferring to the skin. In an alternative embodiment, the cooling agents can be incorporated into a bath tissue which can evoke a sensation of wetness during use of the product.

SUMMARY

The present disclosure is generally directed to dry wiping products and particularly to dry tissue products that, when held against the skin, can provide a cooling sensation. In one embodiment, for instance, the tissue product can comprise a facial tissue. The facial tissue can be used to provide comfort to a user's nose. For example, when suffering from the common cold, a person's nose can become inflamed and sore. In one embodiment, the present disclosure is directed to a tissue product that can not only be used to wipe one's nose, but can also provide the nose with a cooling sensation for providing comfort and relief.

In an alternative embodiment, the tissue product can comprise a bath tissue. The bath tissue, for instance, may comprise a spirally wound product. The bath tissue can also provide a cooling sensation to the user. Of particular advantage, when used as a bath tissue it has unexpectedly been found that the cooling sensation evokes a sensation of wetness which can lead to a perception of improved cleaning.

In one embodiment, for instance, the present disclosure is directed to a tissue product that is made from at least one tissue web containing fibers, such as pulp fibers either alone or in combination with synthetic fibers. The tissue web can have a bulk of at least about 2 cc/g. In accordance with the present disclosure, a temperature change composition is present on at least one side of the tissue web. The temperature change composition comprises at lease one phase change agent that undergoes a phase change at a temperature of from about 20° C. to about 35° C. For instance, in one embodiment, the phase change agent may convert from a solid to a liquid within the above temperature range.

The phase change agent can have a heat of fusion of at least about 35 cal/g, such as at least about 40 cal/g, such as at least about 45 cal/g. The at least one phase change agent is present in the tissue web in an amount such that the finished tissue product has a heat absorption factor of at least about 120 cal/m$^2$, such as at least about 140 cal/m$^2$, such as from about 140 cal/m$^2$ to about 300 cal/m$^2$ or greater. Once contacted with the skin of a user either directly or indirectly, the phase change agent absorbs body heat given off by the user and undergoes a phase change which, in turn, provides a cooling sensation to the skin.

In one embodiment, the phase change agent can be incorporated into the tissue product such that the phase change agent does not directly contact the skin and, therefore, does not transfer to the skin. For example, in one embodiment, the tissue product can include at least two tissue webs that have been attached together. The temperature change composition can be contained in between the two tissue webs.

In an alternative embodiment, the phase change agent may be incorporated into the tissue product so as to directly contact the skin of the user. For instance, in one embodiment, the phase change agent may be applied to an exterior surface of a spirally wound bath tissue product.

The phase change agent incorporated into the temperature change composition can vary depending upon the particular application and the desired result. The phase change agent, for instance, can comprise an oil soluble and hydrophobic material. Examples of phase change agents include hydrocarbons, waxes, oils, fatty acids, fatty acid esters, dibasic acids, dibasic esters, 1-halides, primary alcohols, aromatic compounds, anhydrides, ethylene carbonates, polyhydric alcohols, and mixtures thereof. In one embodiment, for instance, a plurality of phase change agents can be incorporated into the temperature change composition.

Particular examples of phase change agents well suited for use in the present disclosure include octadecane, stearyl heptonoate, nonadecane, and mixtures thereof.

The temperature change composition, in addition to the phase change agent, can contain various other ingredients. For instance, in one embodiment, a carrier may be incorporated into the composition. Carriers that may be included in the composition include various hydrophilic materials. For instance, in one embodiment, the carrier may comprise glycerin.

In addition to the temperature change composition, various other compositions may be incorporated into the tissue product. For example, in one embodiment, in addition to the temperature change composition, the tissue product may contain a lotion composition. The lotion composition, for instance, may be present on an exterior surface of the tissue product for transfer to the skin.

The present disclosure is also directed to a method for soothing or comforting the skin. The method includes the steps of contacting an exterior surface of a tissue sheet with the skin of a user at a particular location. The tissue sheet may contain a temperature change composition as described above. The temperature change composition can be contained in the tissue sheet so as to not substantially reside on the exterior surface of the tissue sheet so as to inhibit transfer to the skin of the user.

The tissue sheet is held in contact with the skin of the user for a period of time sufficient for the temperature change composition to absorb body heat given off by the skin. More particularly, the temperature change composition absorbs sufficient body heat so that the phase change agent undergoes a phase change thereby providing a cooling sensation to the skin.

In one application, the tissue sheet can be placed against the nose of the user for providing soothing relief and comfort to the nose should the nose be irritated or inflamed.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
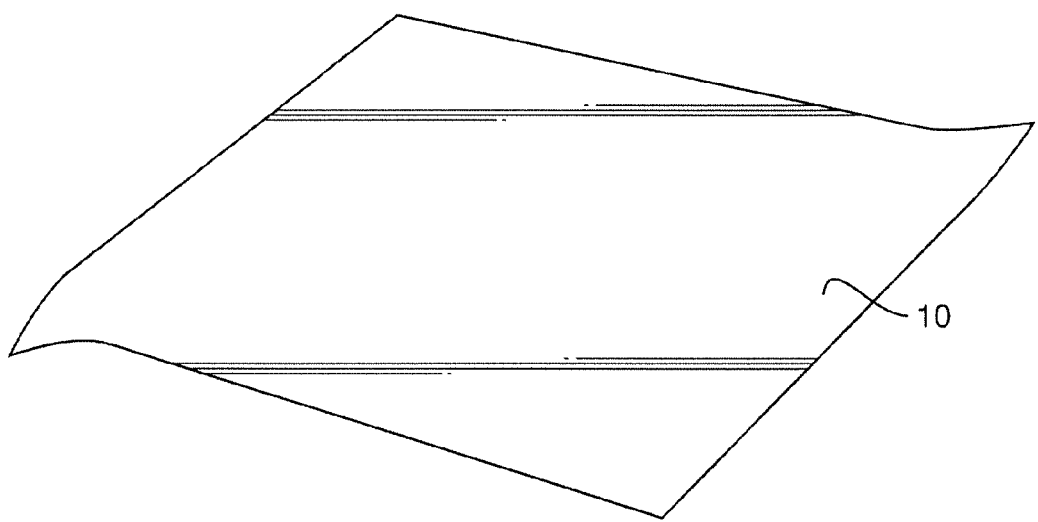
FIG. 1 is a perspective view of one embodiment of a wiping product made in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

Dry, as used herein, to describe tissue or wiping products means that the product is supplied without any moisture beyond the equilibrium moisture that is generally associated with the product. The "equilibrium moisture" is the moisture that the sheet contains when exposed to ambient conditions for extended periods of time. The equilibrium moisture within the sheet will not change with time at the same relative humidity and temperature. The dry products of the present invention will have equilibrium moisture contents typically of less than 15%, such as less than 10% such as from about 3% to about 8% under most ambient conditions that are encountered during routine use of the product.

The heat absorption factor, as used herein, expressed in cal/m$^2$ is defined as the product of the heat of fusion of the cooling composition expressed in cal/gram and the application rate of the cooling composition applied to the tissue product expressed in gram/m$^2$.

Latent heat of fusion and melting points are determined by differential scanning calorimetry (DSC). Melting point, as herein defined, refers to the peak melt temperature as determined by DSC.

The present disclosure is generally directed to dry wiping products, such as dry tissue products, that have improved perceived benefits. In particular, wiping products made in accordance with the present disclosure, when contacted against the skin, can provide a cooling sensation and feeling. The cooling sensation can, for instance, provide comfort and a soothing feeling to irritated skin. It is also found, that when used with a bath tissue, cooling can also evoke a sensation of wetness which can lead to a perception of improved cleaning. In one embodiment, the wiping product can be designed to provide a cooling sensation without having to transfer any chemical composition to the skin of the user.

In one embodiment, for instance, the present disclosure is directed to a dry wiping product, such as a facial tissue product, that contains a temperature change composition. The temperature change composition includes at least one phase change agent that undergoes a phase change when elevated in temperature. The phase change agent, for example, can have a relatively high heat of fusion which allows it to absorb great amounts of thermal energy and to regulate to a lower temperature than the environment. In particular, when the wiping product is heated such as being contacted with one's skin, the phase change agent quickly warms to its melting point. Due to the high heat of fusion, significant amounts of heat can then be absorbed without temperature change until the phase change agent is completely melted. In turn, a cooling sensation is provided to the skin of the user.

Referring to FIG. 1, one embodiment of a tissue product 10 made in accordance with the present disclosure is shown. The tissue product 10 can comprise any suitable base sheet made from various different types of fiber furnishes. The tissue product 10 can also be a single ply product or can contain multiple tissue webs laminated together.

Tissue webs that may be used to construct the tissue product 10, for instance, can generally contain pulp fibers either alone or in combination with other fibers. Each tissue web can generally have a bulk density of at least 2 cc/g, such as at least 3 cc/g.

Fibers suitable for making tissue webs comprise any natural or synthetic cellulosic fibers including, but not limited to nonwoody fibers, such as cotton, abaca, kenaf, sabai grass, flax, esparto grass, straw, jute hemp, bagasse, milkweed floss fibers, and pineapple leaf fibers; and woody or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. No. 4,793,898, issued Dec. 27, 1988 to Laamanen et al.; U.S. Pat. No. 4,594,130, issued Jun. 10, 1986 to Chang et al.; and U.S. Pat. No. 3,585,104. Useful fibers can also be produced by anthraquinone pulping, exemplified by U.S. Pat. No. 5,595,628 issued Jan. 21, 1997, to Gordon et al.

A portion of the fibers, such as up to 50% or less by dry weight, or from about 5% to about 30% by dry weight, can be synthetic fibers such as rayon, polyolefin fibers, polyester fibers, bicomponent sheath-core fibers, multi-component binder fibers, and the like. An exemplary polyethylene fiber is Pulpex®, available from Hercules, Inc. (Wilmington, Del.). Any known bleaching method can be used. Synthetic cellulose fiber types include rayon in all its varieties and other fibers derived from viscose or chemically-modified cellulose.

Chemically treated natural cellulosic fibers can be used such as mercerized pulps, chemically stiffened or crosslinked fibers, or sulfonated fibers. For good mechanical properties in using papermaking fibers, it can be desirable that the fibers be relatively undamaged and largely unrefined or only lightly refined. While recycled fibers can be used, virgin fibers are generally useful for their mechanical properties and lack of contaminants. Mercerized fibers, regenerated cellulosic fibers, cellulose produced by microbes, rayon, and other cellulosic material or cellulosic derivatives can be used. Suitable papermaking fibers can also include recycled fibers, virgin fibers, or mixes thereof. In certain embodiments capable of high bulk and good compressive properties, the fibers can have a Canadian Standard Freeness of at least 200, more specifically at least 300, more specifically still at least 400, and most specifically at least 500.

Other papermaking fibers that can be used in the present disclosure include paper broke or recycled fibers and high yield fibers. High yield pulp fibers are those papermaking fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin. High yield fibers are well known for their stiffness in both dry and wet states relative to typical chemically pulped fibers.

In general, any process capable of forming a tissue web can also be utilized in the present disclosure. For example, a papermaking process of the present disclosure can utilize creping, wet creping, double creping, embossing, wet pressing, air pressing, through-air drying, creped through-air drying, uncreped through-air drying, hydroentangling, air laying, as well as other steps known in the art.

The tissue web may be formed from a fiber furnish containing pulp fibers in an amount of at least about 50% by weight, such as at least about 60% by weight, such as at least about 70% by weight, such as at least about 80% by weight, such as at least about 90% by weight, such as 100% by weight.

Also suitable for products of the present disclosure are tissue sheets that are pattern densified or imprinted, such as the tissue sheets disclosed in any of the following U.S. Pat. No. 4,514,345 issued on Apr. 30, 1985, to Johnson et al.; U.S. Pat. No. 4,528,239 issued on Jul. 9, 1985, to Trokhan; U.S. Pat. No. 5,098,522 issued on Mar. 24, 1992; U.S. Pat. No. 5,260,171 issued on Nov. 9, 1993, to Smurkoski et al.; U.S. Pat. No. 5,275,700 issued on Jan. 4, 1994, to Trokhan; U.S. Pat. No. 5,328,565 issued on Jul. 12, 1994, to Rasch et al.; U.S. Pat. No. 5,334,289 issued on Aug. 2, 1994, to Trokhan et al.; U.S. Pat. No. 5,431,786 issued on Jul. 11, 1995, to Rasch et al.; U.S. Pat. No. 5,496,624 issued on Mar. 5, 1996, to Steltjes, Jr. et al.; U.S. Pat. No. 5,500,277 issued on Mar. 19, 1996, to Trokhan et al.; U.S. Pat. No. 5,514,523 issued on May 7, 1996, to Trokhan et al.; U.S. Pat. No. 5,554,467 issued on Sep. 10, 1996, to Trokhan et al.; U.S. Pat. No. 5,566,724 issued on Oct. 22, 1996, to Trokhan et al.; U.S. Pat. No. 5,624,790 issued on Apr. 29, 1997, to Trokhan et al.; and, U.S. Pat. No. 5,628,876 issued on May 13, 1997, to Ayers et al., the disclosures of which are incorporated herein by reference to the extent that they are non-contradictory herewith. Such imprinted tissue sheets may have a network of densified regions that have been imprinted against a drum dryer by an imprinting fabric, and regions that are relatively less densified (e.g., "domes" in the tissue sheet) corresponding to deflection conduits in the imprinting fabric, wherein the tissue sheet superposed over the deflection conduits was deflected by an air pressure differential across the deflection conduit to form a lower-density pillow-like region or dome in the tissue sheet.

The tissue web can also be formed without a substantial amount of inner fiber-to-fiber bond strength. In this regard, the fiber furnish used to form the base web can be treated with a chemical debonding agent. The debonding agent can be added to the fiber slurry during the pulping process or can be added directly to the headbox. Suitable debonding agents that may be used in the present disclosure include cationic debonding agents such as fatty dialkyl quaternary amine salts, mono fatty alkyl tertiary amine salts, primary amine salts, imidazoline quaternary salts, silicone quaternary salt and unsaturated fatty alkyl amine salts. Other suitable debonding agents are disclosed in U.S. Pat. No. 5,529,665 to Kaun which is incorporated herein by reference. In particular, Kaun discloses the use of cationic silicone compositions as debonding agents.

In one embodiment, the debonding agent used in the process of the present disclosure is an organic quaternary ammonium chloride and, particularly, a silicone-based amine salt of a quaternary ammonium chloride. For example, the debonding agent can be PROSOFT® TQ1003, marketed by the Hercules Corporation. The debonding agent can be added to the fiber slurry in an amount of from about 1 kg per metric tonne to about 10 kg per metric tonne of fibers present within the slurry.

In an alternative embodiment, the debonding agent can be an imidazoline-based agent. The imidazoline-based debonding agent can be obtained, for instance, from the Witco Corporation. The imidazoline-based debonding agent can be added in an amount of between 2.0 to about 15 kg per metric tonne.

In one embodiment, the debonding agent can be added to the fiber furnish according to a process as disclosed in PCT Application having an International Publication No. WO 99/34057 filed on Dec. 17, 1998 or in PCT Published Application having an International Publication No. WO 00/66835 filed on Apr. 28, 2000, which are both incorporated herein by reference. In the above publications, a process is disclosed in which a chemical additive, such as a debonding agent, is adsorbed onto cellulosic papermaking fibers at high levels. The process includes the steps of treating a fiber slurry with an excess of the chemical additive, allowing sufficient residence time for adsorption to occur, filtering the slurry to remove unadsorbed chemical additives, and redispersing the filtered pulp with fresh water prior to forming a nonwoven web.

Optional chemical additives may also be added to the aqueous papermaking furnish or to the formed embryonic web to impart additional benefits to the product and process and are not antagonistic to the intended benefits of the invention. The following materials are included as examples of additional chemicals that may be applied to the web along with the additive composition of the present invention. The chemicals are included as examples and are not intended to limit the scope of the invention. Such chemicals may be added at any point in the papermaking process, including being added simultaneously with the additive composition in the pulp making process, wherein said additive or additives are blended directly with the additive composition.

Additional types of chemicals that may be added to the paper web include, but is not limited to, absorbency aids usually in the form of cationic, anionic, or non-ionic surfactants, humectants and plasticizers such as low molecular weight polyethylene glycols and polyhydroxy compounds such as glycerin and propylene glycol. Materials that supply skin health benefits such as mineral oil, aloe extract, vitamin e, silicone, lotions in general and the like may also be incorporated into the finished products.

In general, the products of the present invention can be used in conjunction with any known materials and chemicals that are not antagonistic to its intended use. Examples of such materials include but are not limited to odor control agents, such as odor absorbents, activated carbon fibers and particles, baby powder, baking soda, chelating agents, zeolites, perfumes or other odor-masking agents, cyclodextrin compounds, oxidizers, and the like. Superabsorbent particles, synthetic fibers, or films may also be employed. Additional options include cationic dyes, optical brighteners, humectants, emollients, and the like.

Tissue webs that may be treated in accordance with the present disclosure may include a single homogenous layer of fibers or may include a stratified or layered construction. For instance, the tissue web ply may include two or three layers of fibers. Each layer may have a different fiber composition Each of the fiber layers comprise a dilute aqueous suspension of papermaking fibers. The particular fibers contained in each layer generally depends upon the product being formed and the desired results. In one embodiment, for instance, a middle layer contains southern softwood kraft fibers either alone or in combination with other fibers such as high yield fibers. The outer layers, on the other hand, can contain softwood fibers, such as northern softwood kraft.

In an alternative embodiment, the middle layer may contain softwood fibers for strength, while the outer layers may comprise hardwood fibers, such as eucalyptus fibers, for a perceived softness.

The basis weight of tissue webs made in accordance with the present disclosure can vary depending upon the final product. For example, the process may be used to produce facial tissues, bath tissues, paper towels, industrial wipers, and the like. In general, the basis weight of the tissue products may vary from about 10 gsm to about 80 gsm, such as from about 20 gsm to about 60 gsm. For bath and facial tissues, for instance, the basis weight may range from about 10 gsm to about 60 gsm. For paper towels, on the other hand, the basis weight may range from about 25 gsm to about 80 gsm.

The tissue web bulk may also vary from about 2 cc/g to 20 cc/g, such as from about 5 cc/g to 15 cc/g. The sheet "bulk" is calculated as the quotient of the caliper of a dry tissue sheet, expressed in microns, divided by the dry basis weight, expressed in grams per square meter. The resulting sheet bulk is expressed in cubic centimeters per gram. More specifically, the caliper is measured as the total thickness of a stack of ten representative sheets and dividing the total thickness of the stack by ten, where each sheet within the stack is placed with the same side up. Caliper is measured in accordance with TAPPI test method T411 om-89 "Thickness (caliper) of Paper, Paperboard, and Combined Board" with Note 3 for stacked sheets. The micrometer used for carrying out T411 om-89 is an Emveco 200-A Tissue Caliper Tester available from Emveco, Inc., Newberg, Oreg. The micrometer has a load of 2.00 kilo-Pascals (132 grams per square inch), a pressure foot area of 2500 square millimeters, a pressure foot diameter of 56.42 millimeters, a dwell time of 3 seconds and a lowering rate of 0.8 millimeters per second.

In multiple ply products, the basis weight of each tissue web present in the product can also vary. In general, the total basis weight of a multiple ply product will generally be the same as indicated above, such as from about 20 gsm to about 80 gsm. Thus, the basis weight of each ply can be from about 5 gsm to about 60 gsm, such as from about 10 gsm to about 40 gsm.

In accordance with the present disclosure, the tissue product 10 contains a temperature change composition. The temperature change composition includes at least one phase change agent that undergoes a phase change when heated which, in turn, provides a cooling sensation to the skin. The temperature change composition can be incorporated into the tissue product 10 using any suitable method or technique. For example, the temperature change composition can be sprayed onto the tissue product, extruded onto the tissue product, or printed onto the tissue product using, for instance, flexographic printing, direct gravure printing, or indirect gravure printing. In still another embodiment, the temperature change composition can be applied to the tissue product using any suitable coating equipment, such as a knife coater or slot coater. As the temperature change composition is solid at room temperature in one embodiment, it may be desirable to melt the composition prior to application to the tissue web. The application of such molten materials to a finished tissue web is well known in the art. At times it may also be advantageous to cool the web directly after application of the molten phase change agent, especially when the treated product is wound into a spirally wound roll either for a finished product or for further processing. The cooling of the web below the melting point of the phase change agent reduces the potential of the spirally wound web from becoming "blocked". "Blocked" as used herein refers to the tendency of adjacent facing sheets in the spirally wound roll to adhere to each other and restrict the ability to unwind the web from the spirally wound roll.

In general, a phase change agent includes any substance that has the capability of absorbing or releasing thermal energy to reduce or eliminate heat flow at or within a temperature stabilizing range. The temperature stabilizing range may include a particular transition temperature or range of transition temperatures. A phase change agent used in conjunction with various aspects of the present disclosure preferably will be capable of altering a flow of thermal energy during a time when the phase change agent is absorbing or releasing heat, typically as the phase change agent undergoes a transition between two states (e.g., liquid and solid states, liquid and gaseous states, solid and gaseous states, or two solid states). This action is typically transient, meaning it will occur until a latent heat of the phase change agent is absorbed or released during a heating or cooling process. Thermal energy may be stored or removed from the phase change agent, and the phase change agent typically can be effectively recharged by a source of heat or cold. For the purposes of the present disclosure, the temperature change compositions of the present invention exhibit a phase change at temperatures between about 23 degrees C. and about 35 degrees C. such as to be appropriate for use in cooling skin. In other embodiments of the present disclosure, materials may be chosen with transition temperatures between about 23 degrees C. and about 32 degrees C., between about 28 degrees C. and about 32 degrees C., or within any other suitable range. The phase change temperature is selected such that the phase change occurs between the ambient temperature of the product and the external temperature of the user's skin.

The temperature change composition of the present disclosure may comprise a mixture of phase change agents that have a mixture of transition temperatures. When a mixture of phase change agents is used, the components can be selected so as to have a collective melting point within the above mentioned limits. In some cases the melting points of the individual phase change agents comprising the temperature change composition may lie outside the melting point limits for the phase change temperature of the temperature change composition. However, the mixture of phase change agents will display a phase change within the desired temperature limits. When the temperature change composition is held against the skin either directly or indirectly, the composition slowly warms to the temperature of the skin from room temperature. The phase change agent melts at its specified phase change temperature. That melting requires heat, which is taken from the skin, imparting a feeling of cooling. Once the material is melted, the cooling sensation dissipates. Having a range of phase change temperatures (melting points in this case) of the phase change agents may extend the range of temperatures where cooling is felt. In one example, a combination of phase change agents having phase change temperatures at 18° C., 28° C., and 35° C. are combined to create a temperature change composition having a melting point between 23° C. and 32° C.

Suitable phase change agents include, by way of example and not by limitation, LURAPRET phase change powder, a purified, encapsulated paraffin available from BASF, hydrocarbons (e.g., straight chain alkanes or paraffinic hydrocarbons, branched-chain alkanes, unsaturated hydrocarbons, halogenated hydrocarbons, and alicyclic hydrocarbons), waxes, fatty acids, fatty acid esters, dibasic acids, dibasic esters, 1-halides, primary alcohols, aromatic compounds, anhydrides (e.g., stearic anhydride), ethylene carbonate, polyhydric alcohols (e.g., 2,2-dimethyl-1,3-propanediol, 2-hydroxymethyl-2-methyl-1,3-propanediol, pentaerythritol, dipentaerythritol, pentaglycerine, tetramethylol ethane, neopentyl glycol, tetramethylol propane, monoaminopentaerythritol, diaminopentaerythritol, and tris(hydroxvmethyl)acetic acid), polymers (e.g., polyethylene, polyethylene glycol, polypropylene, polypropylene glycol, polytetramethylene glycol, and copolymers, such as polyacrylate or poly(meth)acrylate with alkyl hydrocarbon side chain or with polyethylene glycol side chain and copolymers comprising polyethylene, polyethylene glycol, polypropylene, polypropylene glycol, or polytetramethylene glycol), and mixtures thereof. Two well suited phase change agents are stearyl heptanoate and n-octadecane.

As described above, in one embodiment, the temperature change composition may contain a mixture of two or more phase change agents. In one particular embodiment, the temperature change composition comprises a mixture of stearyl heptanoate and n-octadecane.

Phase change agents of the present disclosure may include phase change agents in a non-encapsulated form and phase change agents in an encapsulated form. A phase change agent in a non-encapsulated form may be provided as a solid in a variety of forms (e.g., bulk form, powders, pellets, granules, flakes, and so forth) or as a liquid in a variety of forms (e.g., molten form, dissolved in a solvent, and so forth).

Another aspect of the temperature change compositions of the present invention is the heat of fusion of the temperature change composition comprising the phase change agents. The temperature change compositions of the present disclosure can have heats of fusion of at least about 35 cal/g, such as at least about 40 cal/g, such as at least about 45 cal/g. For instance, in one embodiment, the temperature change composition comprises a hydrocarbon as the phase change agent, such as a straight chain hydrocarbon. The hydrocarbon, for instance, may contain more than about 12 carbon atoms in the chain, such as from about 18 carbon atoms to about 19 carbon atoms in the chain. Particular examples of phase change agents include, for instance, octadecane (heat of fusion of about 57.8 cal/g), nonadecane, stearyl heptonoate, and mixtures thereof.

The one or more phase change agents can be contained in the temperature change composition in an amount from about 1% by weight to 100% by weight, such as from about 50% by weight to about 100% by weight. For example, in particular embodiments, the phase change agents may be present in the temperature change composition in an amount from about 80% by weight to about 100% by weight.

Perhaps more importantly, however, is the heat absorption factor of the products of the current invention. The heat absorption factor, expressed in $cal/m^2$, is the product of the heat of fusion of the temperature change composition expressed in cal/gram and the application rate of the temperature change composition applied to the tissue product expressed in $gram/m^2$. The heat absorption factor of the products of the present disclosure can be at least about 120 $cal/m^2$, such as at least about 140 $cal/m^2$ such as from about 140 $cal/m^2$ to about 300 $cal/m^2$ or greater. For many applications, the temperature change composition can be applied to a tissue web such that the phase change agents are present on the web in an amount from about 4 gsm to about 25 gsm.

In addition to one or more phase change agents, the temperature change composition can contain various other ingredients and components. For instance, in one embodiment, the temperature change composition can contain a carrier. In general, any suitable carrier can be used into which the phase change agents are insoluble. For instance, in one embodiment, a carrier can be used into which the phase change agents are immiscible. The carrier, for example, may be hydrophilic in one embodiment. In general the polarity of the phase change agents and the carrier, if present, can be opposites. Incorporation of materials which are miscible with the phase change agents will tend to impact the melting point of the temperature change composition and reduce the heat of fusion of the temperature change composition. For example, it has been found that stearyl heptanoate, n-octadecane and other hydrophobic phase change agents can not be blended directly into a temperature change composition containing significant amounts of hydrophobic ingredients such as mineral oil, ceresin wax and other ingredients which are routinely used and described for lotioned facial tissue. The hydrophobic lotion ingredients and phase change agents are miscible in one another, and the resultant temperature change composition has a significantly decreased heat of fusion and may fail to produce a detectable cooling sensation during use.

Examples of carriers that may be used include, for instance, a glycerine, including any glycerine derivative. Other carriers may include, for instance, crosslinked copolymers of acrylic acid and C10 to C30 alkyl acrylates.

In addition to a carrier, any other suitable ingredient may be contained in the temperature change composition that does not interfere with the functional properties of the phase change agents. When the temperature change compostion is applied to the exterior surface of the tissue product such that the temperature change composition may directly contact the skin it may be advantageous to incorporate additional moisturizers into the temperature change composition in addition to the phase change agents. When hydrophobic moisturizing agents are used, the moisturizing agent may be incorporated in a manner so as to insure that the temperature composition meets the requirements for heat of fusion and melting point. In one embodiment, a preferred moisturizing agent is a stearyl dimethicone wax such as DC 2503 cosmetic wax commercially available from Dow-Corning in Midland, Mich.

Although the temperature change composition can be present on an exterior surface of the tissue product 10 as shown on FIG. 1, in one embodiment, the temperature change composition can be incorporated into the tissue product in a manner so that substantially none of the temperature change composition is present on the exterior surfaces. For instance, referring to FIG. 2, a tissue product 20 is shown that is comprised of a first tissue web 22 laminated to a second tissue web 24. As shown, positioned in between the first tissue web 22 and the second tissue web 24 is a temperature change composition 26 made in accordance with the present disclosure. By locating the temperature change composition 26 in between the tissue webs, the temperature change composition is substantially prevented from being transferred to a user's skin. When the tissue product 20, however, is held against the skin, body heat will be absorbed by the temperature change composition 26 through the tissue webs thus elevating in temperature. The increase in temperature will cause a phase change to occur in the phase change agent providing a cooling sensation to the skin of the user.

In one specific embodiment the cooling tissue product is a facial tissue comprising three or more plies, two outer plies and one or more interior plies. The temperature change composition is applied to at least one of the one or more interior plies. In another embodiment, the cooling tissue product is a facial tissue comprising two plies, comprising two outer facing surfaces and two oppositely facing inner surfaces. The phase change composition is applied to one or both of the oppositely facing inner surfaces. In another embodiment, the product is a multi-ply tissue product where the phase change composition is applied selectively to the inner portion of the multi-ply product so as to minimize blocking.

In this manner, other beneficial compositions may be applied to the exterior surface of the tissue product and used in conjunction with the temperature change composition 26. For example, in one embodiment, a lotion that is intended to moisturize the skin can be present on at least one exterior surface of the tissue product and may work in conjunction with the temperature change composition. In this manner, the tissue product 20 can not only provide a cooling sensation to the user, but can also transfer a moisturizer to the skin.

In addition to lotions, any other suitable composition may also be applied to the exterior surface. For instance, in one embodiment, various softening agents may be present on the exterior surfaces of the tissue product. One example of a softening agent may comprise a polysiloxane.

Figure 2:
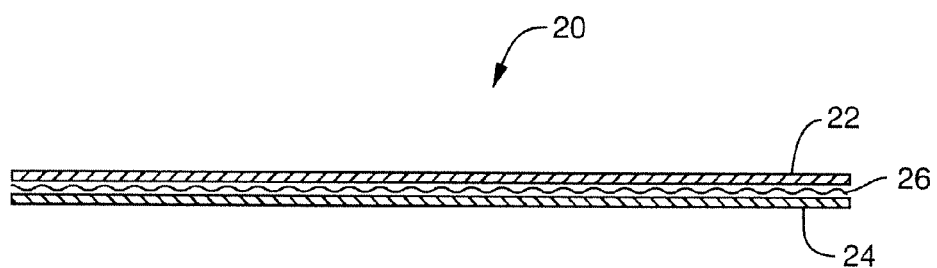
FIG. 2 is a cross-sectional view of the wiping product illustrated in FIG. 1.
Figure 3:
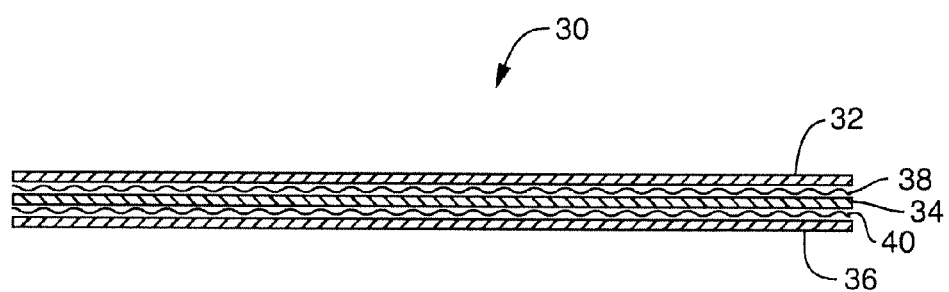
FIG. 3 is a cross-sectional view of another embodiment of a wiping product made in accordance with the present disclosure.

In addition to a 2-ply product as shown in FIG. 2, other tissue products that may be made in accordance with the present disclosure can include more than two plies. For example, a 3-ply tissue product 30 is illustrated in FIG. 3. As shown, the tissue product 30 includes a middle tissue web 34 laminated to outer tissue webs 32 and 36. In accordance with the present disclosure, a temperature change composition is located in between the first tissue web 32 and the middle tissue web 34. A temperature change composition 40 is also positioned in between the middle tissue web 34 and the second outer tissue web 36.

In an alternative embodiment, the temperature change composition of the present disclosure can also be present on one or more exterior surfaces of a tissue product. For instance, referring to FIG. 4, in one embodiment, the temperature change composition can be applied to an exterior surface of a bath tissue product 50. As shown, the bath tissue product 50 comprises a spirally wound product containing individual tissue sheets 52 separated by perforation lines 54. The tissue sheets can include a first exterior surface 56 and a second exterior surface 58. Each tissue sheet may comprise a single ply product or a multi-ply product. In accordance with the present disclosure, the temperature change composition may be present on the first exterior surface 56, on the second exterior surface 58, or on both exterior surfaces.

Figure 4:
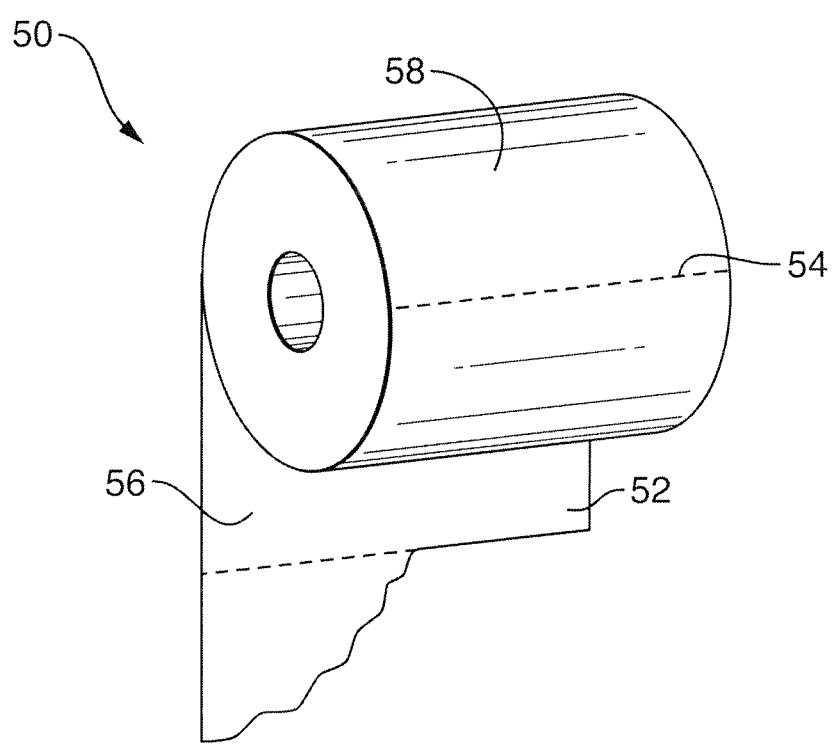
FIG. 4 is a perspective view of one embodiment of a spirally wound bath tissue product made in accordance with the present disclosure.

Applying the temperature change composition to a bath tissue product as shown in FIG. 4 may provide various unexpected benefits and advantages. For example, the temperature change composition may provide a cooling sensation that actually makes the bath tissue sheet evoke a sensation of wetness to the user. The sense of wetness can lead to a perception of improved cleaning.

When applied to a bath tissue as shown in FIG. 4, the temperature change composition may contain a moisturizer as described above so as to provide further benefits to the user.

When hydrophobic phase change agents are used, it may be advantageous to utilize methods to reduce the impact of any hydrophobicity that may develop due to the presence of the hydrophobic phase change agents. A variety of methods are known in the art for reducing hydrophobicity of tissue sheets comprising hydrophobic additives. For example, hydrophilic surfactants having an HLB of greater than 4 may be combined into the temperature change composition as taught in U.S. Pat. No. 6,428,794 B1, "Lotion composition for treating tissue paper". Other exemplary means for reducing the hydrophobicity of the tissue sheet include but is not limited to those taught in U.S. Pat. No. 6,949,167 B2, US20050274470 A1, U.S. Pat. No. 6,896,766 B2, and U.S. Pat. No. 7,008,507 B2 incorporated by reference herein.

EXAMPLES

The present disclosure may be better understood with reference to the following examples.
Analytical:
The latent heat of fusion and melting points of various compositions were determined by differential scanning calorimetry. The samples were analyzed on a TA Instruments DSC 2920 Modulated DSC (Standard Cell) using the following experimental procedure: Approximately 5 mg of the respective material was weighed to the nearest 0.1 mg. Samples were run in the temperature interval from −50° C. to 100° C. with a heating/cooling rate of 10° C./min in an inert gas (N2) atmosphere. The heat of fusion (Hf) was computed from the integral under the respective melting peak, with the reported results being the average value from 3 heating/cooling cycles.

Examples 1-6

The following is a list of temperature change compositions suitable for the present invention. These compositions are comprised of one or more of the following commercially available ingredients:
1) An alkylmethylsiloxane wax (Organofunctional Siloxane) also known as Stearyl Dimethicone, Dow Corning 2503 Cosmetic Wax, which melts on contact with skin and provides moisturizing benefits, 2) Stearyl Heptanoate with a melting point of 23-27 deg C. has a latent Heat of Fusion of around 174 J/g. Stearyl heptanoate is an ester of stearyl alcohol and heptanoic acid (enanthic acid). It is prepared from stearyl alcohol, which may be derived from sperm whale oil or from vegetable sources. Stearyl heptanoate melts on the skin rapidly between 23-27 degrees C. causing cooling of the skin or 3) n-Octadecane, a straight chain saturated hydrocarbon having a melting Point between 28-30° C. and a latent heat of fusion>200 J/g.

| Supplier | Ingredient | | | Average onset melt temp. ° C. | Peak melt temp. ° C. | Average enthalpy J/g |
|---|---|---|---|---|---|---|
| | Stearyl Heptanoate DeGussa Tegosoft ® SH | Octadecane Chevron/ Phillips | Stearyl Dimethicone Dow Corning 2503 Cosmetic Wax | | | |
| Example 1 | 50 | 50 | 0 | 21.5 | 26.1 | 207 |
| Example 2 | 48 | 48 | 4 | 20.8 | 25.6 | 200 |
| Example 3 | 0 | 96 | 4 | 21.1 | 24.4 | 209 |
| Example 4 | 25 | 75 | 0 | 21.4 | 29.7 | 213 |
| Example 5 | 0 | 90 | 10 | 21.1 | 24.8 | 197 |
| Example 6 | 0 | 98 | 2 | 22.7 | 26.3 | 212 |

Example 7

Example 7 demonstrates application of the temperature change composition to a tissue basesheet to produce a facial tissue product having a cooling perception. A three-ply creped tissue sheet having a finished basis weight of 44 g/m2 consisting of 65 percent hardwood and 35 percent softwood fibers was used. Each ply was made from a stratified fiber furnish including two outer layers and a middle layer. Octadecane (Chevron/Phillips) was heated to a temperature of 50° C. and printed on both outer sides of the 3-ply tissue product via a simultaneous offset rotogravure printing process. The fluid reservoirs of the printer were heated to 50° C. to insure the octadecane remained molten throughout the application process. The octadecane was delivered as a 100 percent solids liquid to the sheet. The gravure rolls were electronically engraved, chrome-over-copper rolls supplied by Southern Graphics Systems, located at Louisville, Ky. The rolls had a line screen of 360 cells per lineal inch and a volume of 8 Billion Cubic Microns (BCM) per square inch of roll surface. The rubber backing offset applicator rolls had a 75 Shore A durometer cast polyurethane surface and were supplied by American Roller Company, located at Union Grove, Wis. The process was set up to a condition having 0.375 inch interference between the gravure rolls and the rubber backing rolls and 0.003 inch clearance between the facing rubber backing rolls. The simultaneous offset/offset gravure printer was run at 150'/minute and was found to give an addition rate of 11% octadecane by weight of fiber. The tissue sheet was found to give a pronounced unaided cooling sensation when held in hand or against the face.

Example 8

Example 8 demonstrates the use of phase change agents in conjunction with a topical lotion treatment. A 3-ply lotion facial tissue having a fiber basis weight of 44 g/m2 and containing approximately 8% by weight of a hydrophobic moisturizing lotion comprising mineral oil, stearyl alcohol and ceresin wax was delaminated. To the center ply was applied octadecane at a rate of approximately 15% by weight of total product. The product was then crimped to form a 3-ply facial tissue product having two outer plies comprising a moisturizing lotion applied to the outer facing surfaces of the outer plies and an interior ply comprising a hydrophobic phase change agent. The resultant facial tissue product had a noticeable cool feeling relative to the lotion tissue product not containing the phase change agent.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A dry tissue product comprising:
   a first tissue web comprised of fibers, the tissue web including a first side and a second and opposite side, the tissue web having a bulk of at least about 2 cc/g;
   a temperature change composition comprising a phase change agent that undergoes a phase change at a temperature of from about 20° C. to about 35° C., the phase change agent having a heat of fusion of at least about 35 cal/g and being present in the tissue web such that the tissue web has a heat absorption factor of at least about 120 cal/m$^2$; and
   wherein the temperature change composition is contained in an interior of the tissue product so as to not reside on an exterior surface of the tissue product in order to inhibit transfer of the temperature change composition to the skin of the user, wherein the phase change agent comprises octadecane, stearyl heptanoate, nonadecane, stearyl dimethicone and mixtures thereof.

2. A dry tissue product as defined in claim 1, wherein the tissue product includes a second tissue web and wherein the temperature change composition is located in between the first tissue web and the second tissue web.

3. A dry tissue product as defined in claim 1, wherein the phase change agent is oil soluble and hydrophobic.

4. A dry tissue product as defined in claim 1, wherein the phase change agent comprises, octadecane, stearyl heptanoate, stearyl dimethicone and mixtures thereof.

5. A dry tissue product as defined in claim 1, wherein the phase change agent comprises octadecane.

6. A dry tissue product as defined in claim 1, wherein the phase change agent comprises stearyl heptonoate or nonadecane.

7. A dry tissue product as defined in claim 1, wherein the phase change agent has a heat of fusion of at least about 35 cal/g.

8. A dry tissue product as defined in claim 1, wherein the phase change agent has a heat of fusion of at least about 45 cal/g.

9. A dry tissue product as defined in claim 1, wherein the temperature change composition includes a carrier, the phase change agent being insoluble in the carrier.

10. A dry tissue product as defined in claim 9, wherein the carrier is hydrophilic.

11. A dry tissue product as defined in claim 9, wherein the carrier comprises a glycerin.

12. A dry tissue product as defined in claim 1, further comprising a lotion composition, the lotion composition being located on an exterior surface of the tissue product.

13. A dry tissue product as defined in claim 1, wherein the temperature change composition is present on the tissue web in an amount of from about 5 gsm to about 25 gsm.

14. A dry tissue product as defined in claim 2, wherein the tissue product includes three tissue webs.

15. A dry tissue product as defined in claim 1, wherein the temperature change composition contains a plurality of phase change agents.

16. A dry tissue product as defined in claim 2, wherein the tissue product comprises a facial tissue.

17. A dry tissue product as defined in claim 1, wherein the tissue product comprises a bath tissue containing spirally wound tissue sheets, the temperature change composition being present on an interior surface of the tissue sheets.

18. A dry tissue product as defined in claim 17, wherein the temperature change composition further comprises a moisturizer.

19. A dry tissue product as defined in claim 17, wherein the moisturizer comprises a dimethicone.

20. A method for soothing the skin comprising:
contacting an exterior surface of a tissue sheet with the skin of a user at a particular location, the tissue sheet containing a temperature change composition comprising a phase change agent that undergoes a phase change at a temperature of from about 23° C. to about 32° C., the phase change agent having a heat of fusion of at least about 35 cal/g and being present in the tissue sheet in an amount such that the tissue web has a heat absorption factor of at least about 120 cal/m$^2$, the phase change agent comprising octadecane, stearyl heptanoate, nonadecane, stearyl dimethicone and mixtures thereof,
wherein the temperature change composition is contained in an interior of the tissue sheet so as to not reside on the exterior surface in order to inhibit transfer of the temperature change composition to the skin of the user; and
holding the tissue sheet in contact with the skin an amount of time sufficient for heat transfer to take place from the user to the tissue sheet so as to cause the phase change agent to undergo a phase change thereby causing a cooling sensation on the skin.

21. A method as defined in claim 20, wherein the tissue sheet comprises a plurality of tissue webs, the temperature change composition being located in between two opposing webs.

22. A method as defined in claim 20, wherein the phase change agent comprises octadecane, stearyl heptanoate, stearyl dimethicone or mixtures thereof.

23. A method as defined in claim 20, wherein the tissue sheet is contacted with a nose of the user.

24. A method as defined in claim 20, wherein the temperature change composition is contained in the tissue sheet in an amount from about 5 gsm to about 25 gsm.

25. A dry bath tissue product comprising:
a plurality of tissue sheets separated by perforation lines, the tissue sheets being spirally wound to form a roll, the tissue sheets including a first exterior surface and a second exterior surface; and
a temperature change composition contained in an interior of the tissue product so as to not reside on the exterior surfaces of the tissue product in order to inhibit transfer of the temperature change composition to the skin of the user, the temperature change composition comprising a phase change agent that undergoes a phase change at a temperature of from about 20° C. to about 35° C., the phase change agent having a heat of fusion of at least about 35 cal/g and being present on the tissue sheets such that the tissue sheets have a heat absorption factor of at least about 120 cal/m$^2$, the phase change agent comprising octadecane, stearyl heptanoate, nonadecane, stearyl dimethicone and mixtures thereof.

26. A dry bath tissue product as defined in claim 25, wherein the temperature change composition further comprises a moisturizer.

27. A dry bath tissue product as defined in claim 26, wherein the phase change agent comprises octadecane, stearyl heptanoate, or mixtures thereof combined with stearyl dimethicone.

28. A method for creating the perception of moisture in a dry bath tissue product comprising contacting an exterior surface of a dry bath tissue with a perineal skin, the dry tissue containing a temperature change composition contained in an interior of the tissue product so as to not reside on an exterior surface of the tissue product in order to inhibit transfer of the temperature change composition to the skin of the user, the tissue product comprising a phase change agent that undergoes a phase change at a temperature of from about 23° C. to about 32° C., the phase change agent having a heat of fusion of at least about 35 cal/g and being present in the dry bath tissue in an amount such that the bath tissue has a heat absorption factor of at least about 120 cal/m$^2$, the phase change agent comprising octadecane, stearyl heptanoate, nonadecane, stearyl dimethicone and mixtures thereof.

* * * * *